US008454589B2

(12) United States Patent
Deno et al.

(10) Patent No.: US 8,454,589 B2
(45) Date of Patent: Jun. 4, 2013

(54) SYSTEM AND METHOD FOR ASSESSING EFFECTIVE DELIVERY OF ABLATION THERAPY

(75) Inventors: Don Curtis Deno, Andover, MN (US); Stephan P. Miller, Vadnais Heights, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 783 days.

(21) Appl. No.: 12/622,626

(22) Filed: Nov. 20, 2009

(65) Prior Publication Data

US 2011/0125150 A1     May 26, 2011

(51) Int. Cl.
*A61B 18/04*     (2006.01)

(52) U.S. Cl.
USPC ............................................. 606/34

(58) Field of Classification Search
USPC ............................... 606/27, 34, 41
See application file for complete search history.

(56) References Cited

U.S. PATENT DOCUMENTS

| 5,546,940 | A * | 8/1996 | Panescu et al. ............... 600/374 |
| 6,918,906 | B2 * | 7/2005 | Long ................................. 606/41 |
| 6,936,047 | B2 * | 8/2005 | Nasab et al. ..................... 606/34 |
| 7,001,383 | B2 | 2/2006 | Keidar |
| 7,263,397 | B2 | 8/2007 | Hauck et al. |
| 7,386,339 | B2 | 6/2008 | Strommer et al. |
| 2004/0078036 | A1 * | 4/2004 | Keidar ............................ 606/41 |
| 2005/0203394 | A1 | 9/2005 | Hauck |
| 2006/0184163 | A1 * | 8/2006 | Breen et al. ...................... 606/20 |
| 2007/0049827 | A1 | 3/2007 | Donaldson |
| 2007/0078325 | A1 * | 4/2007 | Fuimaono et al. ............ 600/407 |
| 2007/0129633 | A1 | 6/2007 | Lee et al. |
| 2008/0161788 | A1 | 7/2008 | Dando et al. |
| 2009/0163904 | A1 | 6/2009 | Miller et al. |
| 2009/0171345 | A1 | 7/2009 | Miller et al. |
| 2009/0196480 | A1 | 8/2009 | Nields et al. |
| 2010/0069921 | A1 | 3/2010 | Miller et al. |
| 2010/0228247 | A1 | 9/2010 | Paul et al. |

FOREIGN PATENT DOCUMENTS

WO     WO-2009/065140     5/2009

* cited by examiner

*Primary Examiner* — Michael Peffley
*Assistant Examiner* — Daniel Fowler
(74) *Attorney, Agent, or Firm* — Dykema Gossett PLLC

(57) ABSTRACT

A system and method for assessing effective delivery of ablation therapy to a tissue in a body is provided. A three-dimensional anatomical map of the tissue is generated and displayed with the map defining a corresponding volume. An index is generated corresponding to a location within the volume with the index indicative of a state of ablation therapy at the location. The index may be derived from one or more factors such as the duration an ablation electrode is present at the location, the amount of energy provided, the degree of electrical coupling between an ablation electrode and the tissue at the location and temperature. A visual characteristic (e.g., color intensity) of a portion of the anatomical map corresponding to the location is then altered responsive to the index.

19 Claims, 4 Drawing Sheets

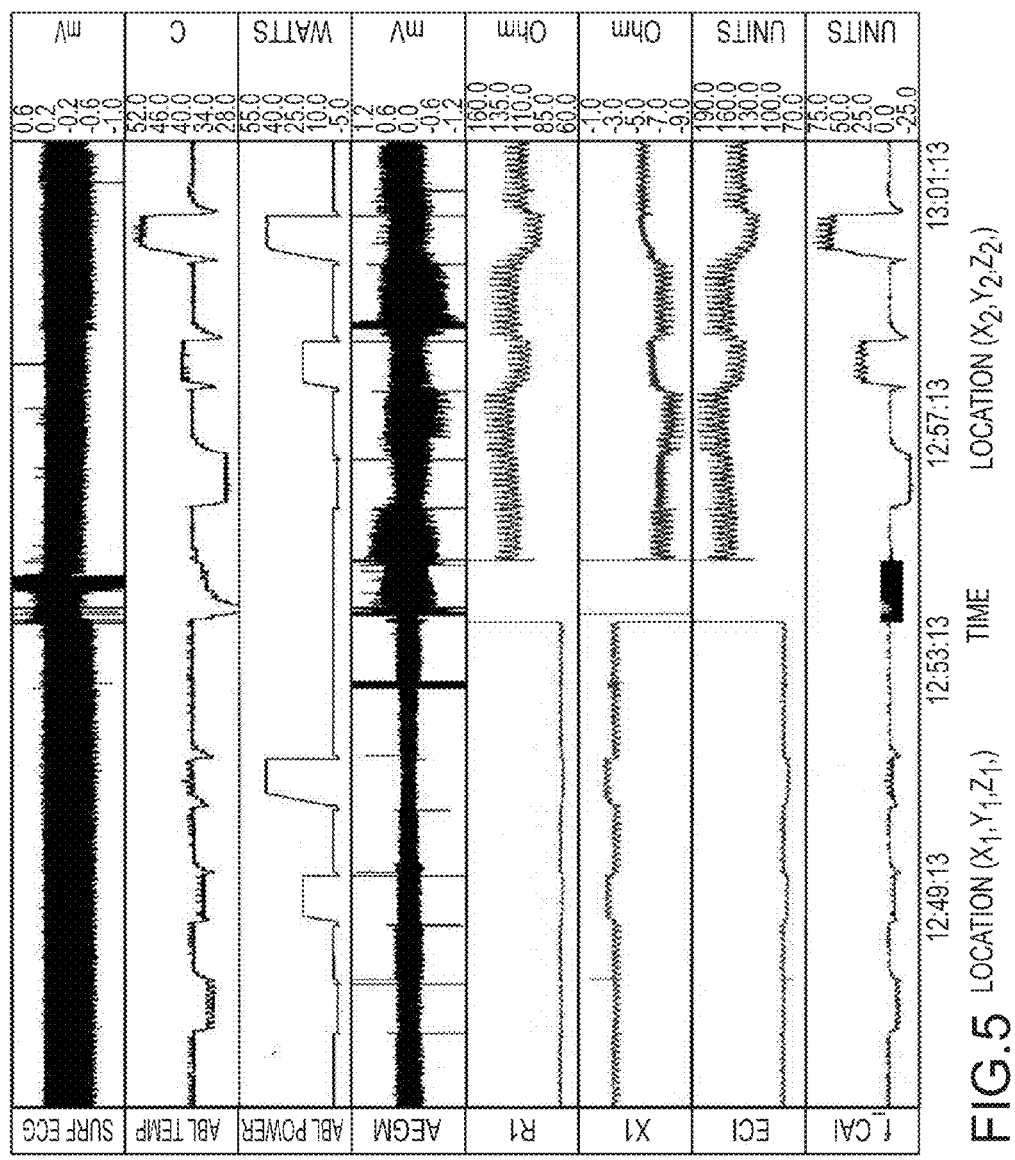

SYSTEM AND METHOD FOR ASSESSING EFFECTIVE DELIVERY OF ABLATION THERAPY

BACKGROUND OF THE INVENTION a. Field of the Invention

This invention relates to a system and method for assessing the effective delivery of ablation therapy to tissue in a body. In particular, the instant invention relates to a system and method for generating and displaying an anatomical map of the tissue and altering a visual characteristic of a portion of the map responsive to an index indicative of the state of ablation therapy.

b. Background Art

Ablation catheters are commonly used to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Electroanatomical mapping systems are frequently used during cardiac ablation procedures to generate a visual representation, or anatomical map, of the endocardial surface. This visual representation permits a clinician to track the locations at which ablation therapy is provided and to view the cardiac structure and ablative lesions from a variety of angles. Tracking ablation delivery sites is important because it is often necessary to achieve a contiguous line of necrosis to disrupt undesirable electrical pathways in the tissue—despite the fact that ablation therapy often involves multiple applications of energy at discrete locations.

Conventional anatomical mapping systems used during ablation procedures require the clinician to manually mark treatment regions on the anatomical map. In particular, the clinician provides an input through a conventional input device (e.g., a mouse, keyboard, etc.) to indicate the location or locations on the map at which ablation lesions have been created. This subjective marking occurs despite numerous variabilities including movement of the ablation catheter and heart due to cardiac contractions, ventilation and movements of the clinician and variation in the application of ablative energy resulting, for example, from changing temperature or impedance levels. As a result, there may not be a strong correlation between lesions marked on the anatomical map by the clinician and the effective delivery of ablation therapy. Clinicians therefore frequently engage in repeated and relatively time consuming electrophysiologic mapping procedures to identify locations where additional ablation therapy is required and then provide additional ablative energy to those locations—often in a repeated cycle. These problems are exacerbated for those clinicians who engage in procedures whereby the ablation catheter is intentionally moved (or "dragged") while generating ablative energy. This type of procedure can help reduce collateral tissue damage and is more time efficient, but increases the odds that manual marking of lesion sites will be inaccurate.

The inventors herein have recognized a need for a system and method for assessing the effective delivery of ablation therapy to tissue in a body that will minimize and/or eliminate one or more of the above-identified deficiencies.

BRIEF SUMMARY OF THE INVENTION

It is desirable to provide a system and method for assessing the effective delivery of ablation therapy to tissue in a body. In particular, it is desirable to be able to alter an anatomical map in an objective fashion to indicate the effective delivery of ablation therapy to tissue.

A system for assessing the effective delivery of ablation therapy to tissue in a body in accordance with one embodiment of the present teachings includes an electronic control unit configured to generate a three-dimensional anatomical map of the tissue. The map defines a corresponding volume. The system further includes a display configured to display the anatomical map. The electronic control unit is further configured to generate an index corresponding to a location within the volume. The index is indicative of a state of ablation therapy at the location. In accordance with various embodiments of the present teachings, the index may be determined responsive to various factors including, for example, the duration of time during which ablation energy is provided at the location, the amount of ablation energy delivered by the ablation catheter at the location, the temperature at or near the location and the degree of contact or electrical coupling between an ablation electrode and the tissue. The electronic control unit is further configured to alter, responsive to the index, a visual characteristic of a portion of the anatomical map corresponding to the location. In one embodiment according to the present teachings, the volume is divided into a plurality of voxels (volume elements) and the altered portion of the anatomical map comprises one of the voxels containing the location. In another embodiment according to the present teachings, the anatomical map defines a surface and the altered portion of the map comprises a part of the surface that is altered responsive to the index and a distance between the location and the part of the surface.

A method for assessing the effective delivery of ablation therapy to tissue in a body in accordance with another embodiment of the present teachings includes the step of generating a three-dimensional anatomical map of the tissue. The map defines a corresponding volume. The method further includes the step of displaying the anatomical map. The method further includes the step of generating an index corresponding to a location within the volume, the index indicative of a state of ablation therapy at the location. The method further includes the step of altering, responsive to the index, a visual characteristic of a portion of the anatomical map corresponding to the location.

The above-described system and method are advantageous because they provide a less subjective and more accurate map of ablation lesions than conventional systems. The use of an index based on one or more factors or predictors indicative of the state of ablative therapy provides a more objective assessment of the effective delivery of ablation therapy while reducing the impact of variabilities such as catheter or tissue movement or changes in operating conditions. As a result, clinicians can assess the effectiveness of ablation therapy with greater confidence and reduce or eliminate the need for electrophysiologic mapping procedures and repeated ablation.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 5 is a series of timing diagrams illustrating variations over time in several factors that may be used in an index to indicate effective delivery of ablation therapy.

DETAILED DESCRIPTION OF EMBODIMENTS OF THE INVENTION

Figure 1:
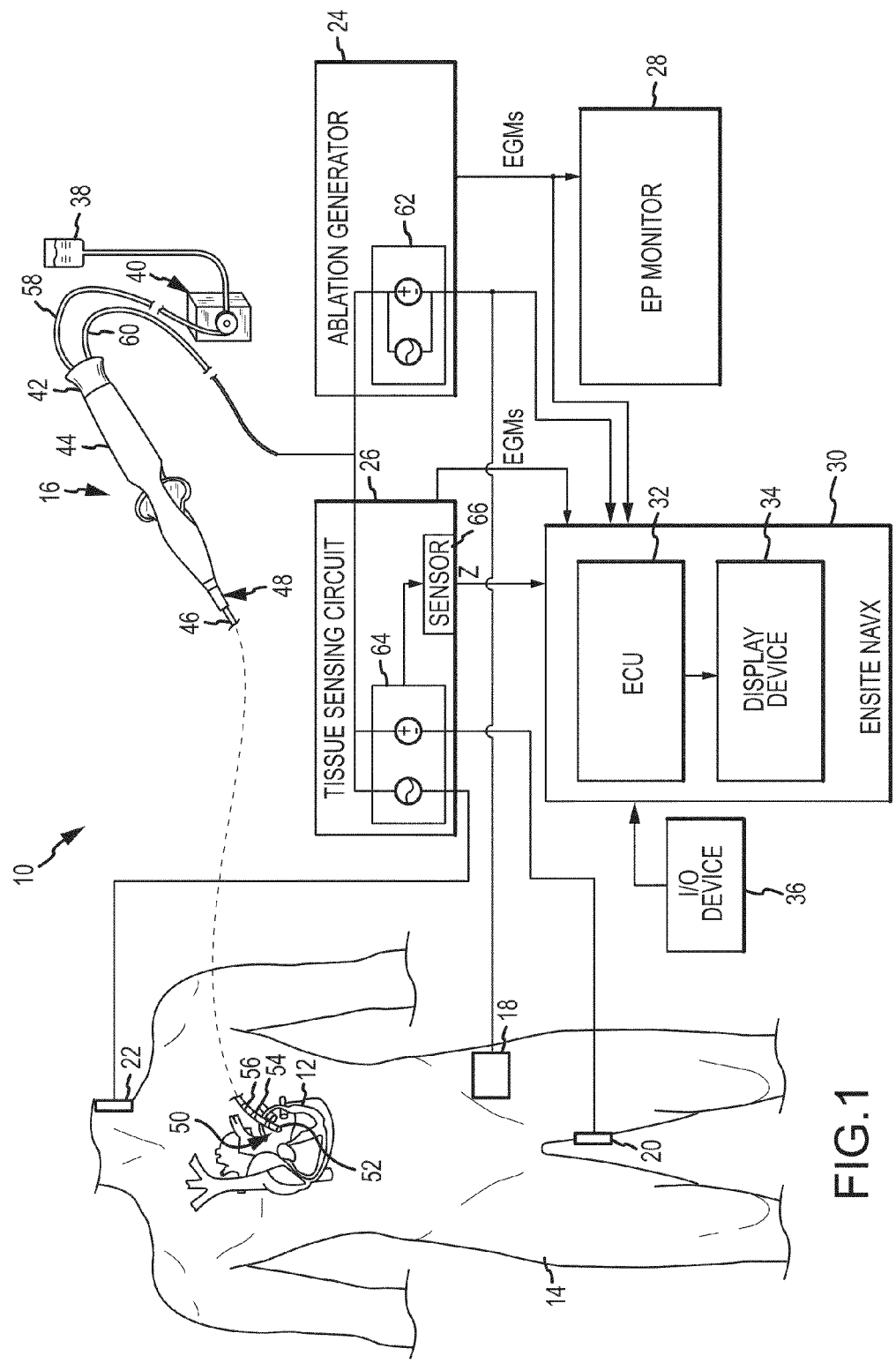
FIG. 1 is diagrammatic view of a system in accordance with the present teachings.

Referring now to the drawings wherein like reference numerals are used to identify identical components in the various views, FIG. 1 illustrates one embodiment of a system 10 for one or more diagnostic and therapeutic functions including components providing an assessment of the effective delivery of ablation therapy to tissue 12 in a body 14. In the illustrated embodiment, tissue 12 comprises heart or cardiac tissue. It should be understood, however, that the present invention may be used to assess effective delivery of ablation therapy to a variety of body tissues. System 10 may include an ablation catheter 16, patch electrodes 18, 20, 22, an ablation generator 24, a tissue sensing circuit 26, an electrophysiology (EP) monitor 28 and a system 30 for visualization, mapping and navigation of internal body structures which may include an electronic control unit 32 in accordance with the present invention, a display device 34 and an input/output (I/O) device 36 among other components.

Catheter 16 is provided for examination, diagnosis and treatment of internal body tissues such as tissue 12. In accordance with one embodiment of the present teachings, catheter 16 comprises an ablation catheter. Catheter 16 may comprise, for example, an ablation catheter of the type sold commercially by St. Jude Medical, Inc. under the "SAFIRE" or "COOL PATH" trademarks and having a four millimeter tip that may be deflected in one direction (uni-directional) or multiple directions (bi-directional). In accordance with one embodiment of the present teachings, catheter 16 comprises an irrigated radio-frequency (RF) ablation catheter. It should be understood, however, that the present invention can be implemented and practiced regardless of the type of ablation energy provided (e.g., cryoablation, ultrasound, etc.). Catheter 16 is connected to a fluid source 38 having a biocompatible fluid such as saline through a pump 40 (which may comprise, for example, a fixed rate roller pump or variable volume syringe pump with a gravity feed supply from fluid source 38 as shown) for irrigation. Catheter 16 is also electrically connected to ablation generator 24 for delivery of RF energy. Catheter 16 may include a cable connector or interface 42, a handle 44, a shaft 46 having a proximal end 48 and a distal 50 end (as used herein, "proximal" refers to a direction toward the end of the catheter near the clinician, and "distal" refers to a direction away from the clinician and (generally) inside the body of a patient) and one or more electrodes 52, 54, 56. Catheter 16 may also include other conventional components not illustrated herein such as a temperature sensor, additional electrodes, and corresponding conductors or leads.

Connector 42 provides mechanical, fluid and electrical connection(s) for cables 58, 60 extending from pump 40 and ablation generator 24. Connector 42 is conventional in the art and is disposed at a proximal end of catheter 16.

Handle 44 provides a location for the clinician to hold catheter 16 and may further provides means for steering or guiding shaft 46 within body 14. For example, handle 44 may include means to change the length of a guidewire extending through catheter 14 to distal end 50 of shaft 46 to steer shaft 46. Handle 44 is also conventional in the art and it will be understood that the construction of handle 44 may vary.

Shaft 46 is an elongated, tubular, flexible member configured for movement within body 14. Shaft 46 support electrodes 52, 54, 56 associated conductors, and possibly additional electronics used for signal processing or conditioning. Shaft 46 may also permit transport, delivery and/or removal of fluids (including irrigation fluids and bodily fluids), medicines, and/or surgical tools or instruments. Shaft 46 may be made from conventional materials such as polyurethane and defines one or more lumens configured to house and/or transport electrical conductors, fluids or surgical tools. Shaft 46 may be introduced into a blood vessel or other structure within body 14 through a conventional introducer. Shaft 46 may then be steered or guided through body 14 to a desired location such as tissue 12 with guide wires or other means known in the art.

Electrodes 52, 54, 46 are provided for a variety of diagnostic and therapeutic purposes including, for example, electrophysiological studies, catheter identification and location, pacing, cardiac mapping and ablation. In the illustrated embodiment, catheter 16 includes an ablation tip electrode 52 at distal end 50 of shaft 46 and a pair of ring electrodes 54, 56. It should be understood, however, that the number, orientation and purpose of electrodes 52, 54, 56 may vary.

Patch electrodes 18, 20, 22 provide RF or navigational signal injection paths and/or are used to sense electrical potentials. Electrodes 18, 20, 22 may also have additional purposes such as the generation of an electromechanical map. Electrodes 18, 20, 22 can be made from flexible, electrically conductive material and be configured for affixation to body 14 such that electrodes 18, 20, 22 are in electrical contact with the patient's skin. Alternatively, electrodes 18, 20, 22 can be part of a pad or support placed under the patient. Electrode 18 may function as an RF indifferent/dispersive return for the RF ablation signal. Electrodes 20, 22 may function as returns for the RF ablation signal source and/or an excitation signal generated by tissue sensing circuit 26 as described in greater detail hereinbelow. Electrodes 20, 22 are preferably spaced relatively far apart for a purpose described hereinbelow. In the illustrated embodiment, electrodes 20, 22, are located on the medial aspect of the left leg and the dorsal aspect of the neck. Electrodes 20, 22, may alternatively be located on the front and back of the torso or in other conventional orientations.

Ablation generator 24 generates, delivers and controls RF energy used by ablation catheter 16. Generator 24 is conventional in the art and may comprise the commercially available unit sold under the model number IBI-1500T RF Cardiac Ablation Generator, available from Irvine Biomedical, Inc. Generator 24 includes an RF ablation signal source 62 configured to generate an ablation signal that is output across a pair of source connectors: a positive polarity connector SOURCE (+) which may connect to tip electrode 52; and a negative polarity connector SOURCE(−) which may be electrically connected by conductors or lead wires to one of patch electrodes 18, 20, 22 (see FIG. 2). It should be understood that the term connectors as used herein does not imply a particular type of physical interface mechanism, but is rather broadly contemplated to represent one or more electrical nodes. Source 62 is configured to generate a signal at a predetermined frequency in accordance with one or more specified parameters (e.g., power, time, etc.) and under the control of various feedback sensing and control circuitry as is know in the art. Source 62 may generate a signal, for example, with a frequency of about 450 kHz or greater. Generator 24 may also monitor various parameters associated with the ablation procedure including impedance, the temperature at the tip of the catheter, ablation energy and the position of the catheter and provide feedback to EP monitor 28 and system 30.

Tissue sensing circuit 26 provides a means, such as tissue sensing signal source 64, for generating an excitation signal used in impedance measurements and means, such as complex impedance sensor 66, for resolving the detected impedance into its component parts. Signal source 64 is configured to generate an excitation signal across source connectors SOURCE (+) and SOURCE (−) (See FIG. 2). Source 64 may output a signal having a frequency within a range from about 1 kHz to over 500 kHz, more preferably within a range of about 2 kHz to 200 kHz, and even more preferably about 20 kHz. In one embodiment, the excitation signal is a constant current signal, preferably in the range of between 20-200 µA, and more preferably about 100 µA. As discussed below, the constant current AC excitation signal generated by source 64 is configured to develop a corresponding AC response voltage signal that is dependent on the complex impedance of tissue 12 and is sensed by complex impedance sensor 66. Sensor 66 resolves the complex impedance into its component parts (i.e., the resistance (R) and reactance (X) or the impedance magnitude (|Z|) and phase angle (∠Z or φ)). Sensor 66 may include conventional filters (e.g., bandpass filters) to block frequencies that are not of interest, but permit appropriate frequencies, such as the excitation frequency, to pass as well as conventional signal processing software used to obtain the component parts of the measured complex impedance.

It should be understood that the excitation signal from source 64 may alternatively be an AC voltage signal where the response signal comprises an AC current signal. It should also be appreciated that the excitation signal frequency is preferably outside of the frequency range of the RF ablation signal, which allows the complex impedance sensor 66 to more readily distinguish the two signals, and facilitates filtering and subsequent processing of the AC response voltage signal. The excitation signal frequency is also preferably outside the frequency range of conventionally expected electrogram (EGM) signals in the frequency range of 0.05-1 kHz. Thus, in summary, the excitation signal preferably has a frequency that is preferably above the typical EGM signal frequencies and below the typical RF ablation signal frequencies.

Circuit 26 is also connected, for a purpose described hereinbelow, across a pair of sense connectors: a positive polarity connector SENSE (+) which may connect to tip electrode 52; and a negative polarity connector SENSE (−) which may be electrically connected to one of patch electrodes 18, 20, 22 (see FIG. 2; note, however, that the connector SENSE (−) should be connected to a different electrode of electrodes 18, 20, 22 relative to the connector SOURCE (−) as discussed below) or another electrode 54, 56 on catheter 16, such as ring electrode 54 as described in commonly assigned U.S. patent application Ser. No. 11/966,232 filed on Dec. 28, 2007 and titled "System and Method for Measurement of an Impedance Using a Catheter Such as an Ablation Catheter," the entire disclosure of which is incorporated herein by reference. It should again be understood that the term connectors as used herein does not imply a particular type of physical interface mechanism, but is rather broadly contemplated to represent one or more electrical nodes.

Figure 2:
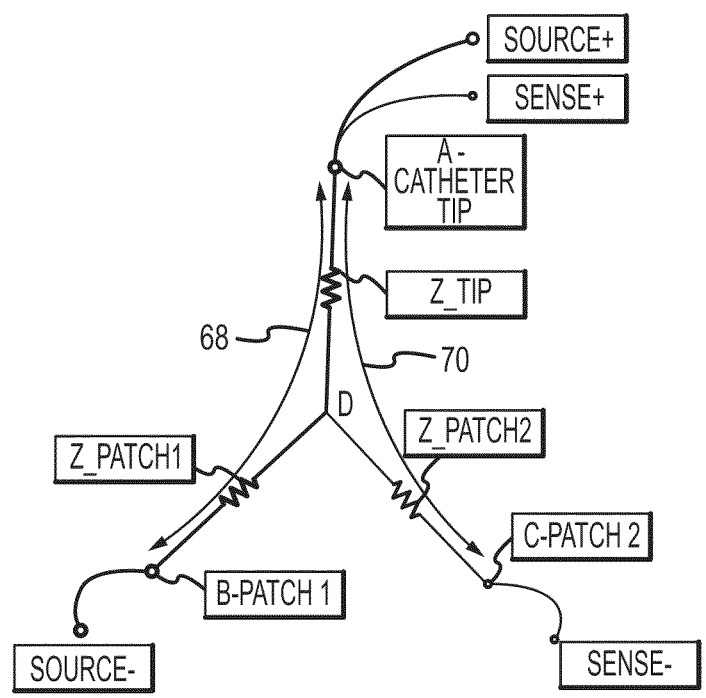
FIG. 2 is a simplified schematic diagram illustrating how a degree of electrical coupling between an electrode and tissue may be determined.

Referring now to FIG. 2, connectors SOURCE (+), SOURCE (−), SENSE (+) and SENSE (−) form a three terminal arrangement permitting measurement of the complex impedance at the interface of tip electrode 52 and tissue 12. Complex impedance can be expressed in rectangular coordinates as set forth in equation (1):

$$Z = R + jX \quad (1)$$

where R is the resistance component (expressed in ohms); and X is a reactance component (also expressed in ohms). Complex impedance can also be expressed polar coordinates as set forth in equation (2):

$$Z = r \cdot e^{j\theta} = |Z| \cdot e^{j \angle Z} \quad (2)$$

where |Z| is the magnitude of the complex impedance (expressed in ohms) and ∠Z=θ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees. The three terminals comprise: (1) a first terminal designated "A-Catheter Tip" which is the tip electrode 52; (2) a second terminal designated "B-Patch 1" such as source return patch electrode 22; and (3) a third terminal designated "C-Patch 2" such as the sense return patch electrode 20. In addition to the ablation (power) signal generated by source 62 of ablation generator 24, the excitation signal generated by source 64 in tissue sensing circuit 26 is also applied across the source connectors (SOURCE (+), SOURCE (−)) for the purpose of inducing a response signal with respect to the load that can be measured and which depends on the complex impedance. As described above, in one embodiment, a 20 kHz, 100 µA AC constant current signal is sourced along the path 68, as illustrated, from one connector (SOURCE (+), starting at node A) through the common node (node D) to a return patch electrode (, SOURCE (−), node B). The complex impedance sensor 66 is coupled to the sense connectors (SENSE (+), SENSE (−)), and is configured to determine the impedance across the path 70. For the constant current excitation signal of a linear circuit, the impedance will be proportional to the observed voltage developed across SENSE (+)/SENSE(−), in accordance with Ohm's Law: Z=V/I. Because voltage sensing is nearly ideal, the current flows through the path 68 only, so the current through path 70 (node D to node C) due to the excitation signal is effectively zero. Accordingly, when measuring the voltage along path 70, the only voltage observed will be where the two paths intersect (i.e. from node A to node D). Depending on the degree of separation of the two patch electrodes (i.e., those forming nodes B and C), an ever-increasing focus will be placed on the tissue volume nearest the tip electrode 52. If the patch electrodes are physically close to each other, the circuit pathways between the catheter tip electrode 52 and the patch electrodes will overlap significantly and impedance measured at the common node (i.e., node D) will reflect impedances not only at the interface of the catheter electrode 52 and tissue 12, but also other impedances between tissue 12 and the surface of body 14. As the patch electrodes are moved further part, the amount of overlap in the circuit paths decreases and impedance measured at the common node is only at or near the tip electrode 52 of catheter 16.

Referring again to FIG. 1, EP monitor 28 is provided to display electrophysiology data including, for example, an electrogram. Monitor 28 is conventional in the art and may comprise an LCD or CRT monitor or another conventional monitor. Monitor 28 may receive inputs from ablation generator 24 as well as other conventional EP lab components not shown in the illustrated embodiment.

System 30 is provided for visualization, mapping and navigation of internal body structures. System 30 may comprise the system having the model name EnSite NavX™ and commercially available from St. Jude Medical., Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference. Alternatively, system 30 may comprise the system sold under the name Carto™ and commercially available from Biosense Webster, Inc. or a magnetic location system such as the system sold under the name gMPS and commercially available from Mediguide Ltd. and as generally shown with reference to U.S. Pat. No. 7,386,339 entitled "Medical Imaging and Navigation System", the entire disclosure of which is incorporated herein by reference. System 30 may include electronic control unit (ECU) 32, display device 34 and I/O device 36 among other components.

ECU 32 is provided to generate anatomical maps of tissue 12, to generate an index indicative of a state of ablation therapy at a location within a volume defined by an anatomical map and to alter a visual characteristics of at least a portion of an anatomical map corresponding to the location. ECU 32 preferably comprises a programmable microprocessor or microcontroller, but may alternatively comprise an application specific integrated circuit (ASIC). ECU 32 may include a central processing unit (CPU) and an input/output (I/O) interface through which ECU 32 may receive a plurality of input signals including signals from sensor 66 of tissue sensing circuit 26, from ablation generator 24 and from I/O device 36 and generate a plurality of output signals including those used to control display device 34. In accordance with one aspect of the present invention, ECU 32 may be programmed with a computer program (i.e., software) encoded on a computer storage medium for performing one or more of the above functions.

Figure 3:
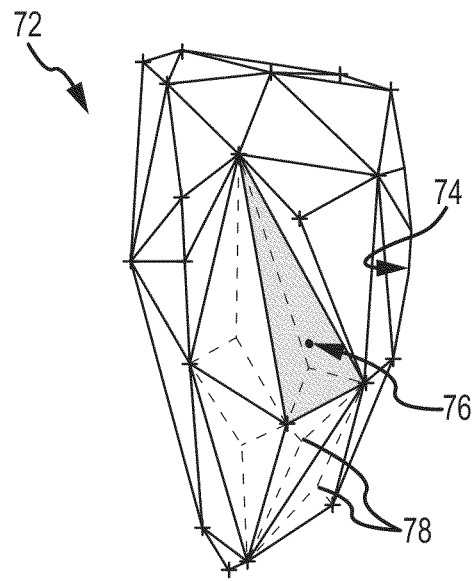
FIG. 3 is a screen display illustrating one embodiment of an anatomical map altered in accordance with the present teachings.

Referring to FIG. 3, ECU 32 generates a three-dimensional anatomical map 72 for illustration on display device 34 in a conventional manner. A plurality of electrodes at one end of catheter 16 or a conventional mapping catheter may be moved within the heart chambers by the clinician while the heart is beating. The locations of the catheter electrodes are measured, for example, using patch electrodes 18, 20, 22 or another sensor (e.g., a magnetic sensor (not shown)) and stored by ECU 32 as a "cloud" of points. A conventional algorithm such as a convex hull algorithm is used to construct a surface around the cloud. The most exterior points are used to create a "shell" representing the shape of the heart. Additional sampling and smoothing operations are then performed to generate the anatomical map 72 shown in FIG. 3. A more detailed explanation of the mapping process is described in the above-referenced U.S. Pat. No. 7,263,397 titled "Method and Apparatus for Catheter Navigation and Location and Mapping in the Heart," the entire disclosure of which is incorporated herein by reference. It should also be understood that ECU 32 could generate map 72 based on a real-time image such as an ultrasound image or fluoroscopic image or a pre-acquired image (e.g., an image generated by an MRI, CT, ultrasound or fluoroscopic system).

Three-dimensional map 72 defines a volume 74 comprising the space within its surface boundaries. ECU 32 is further configured generate an index (CAI) indicative of a state of ablation therapy at a location, such as location 76, within the volume 74. The index is derived from one or more of a plurality of factors indicative of delivery of ablative therapy to tissue 12. These factors may include a duration of time during which ablation tip electrode 52 is present at the location or ablation therapy is provided at the location. As noted above, the location of electrode 52 can be tracked by ECU 32 by reading voltage levels on electrodes 18, 20, 22. Another factor may be the amount of ablation energy provided at the location. This information can be obtained from ablation generator 24 as a measurement of RF power in the case of radio-frequency ablation and will vary based on programmed instructions for delivery of energy and feedback control such as temperature measurements (to avoid charring or steam pops) and impedance measurements (to minimize coagulum formation). Another factor is the temperature proximate the distal end 50 of catheter 16 where tip electrode 52 is located. The temperature can be measured using a conventional temperature sensor (not shown) on the distal end of shaft 46 of catheter 16. Other exemplary factors include an impedance measurement or a change in amplitude in an electrogram both as measured by generator 24. Additional factors may include the flow of irrigation fluid in catheter 16 as measured by a conventional flow sensor or meter (not shown) or the orientation of electrode 52 relative to tissue 12 which could be measured by a force vector sensor (not shown) on catheter 16 or through impedance measurements. Another factor indicative of the state of ablative therapy is contact pressure between electrode 52 and tissue 12 which can be measured through a conventional pressure sensor (not shown).

Another factor that is indicative of effective delivery of ablation therapy and that may be used in the index CAI is the degree of coupling, and particularly electrical coupling, between electrode 52 and tissue 12. As discussed in greater detail hereinabove, ECU 32 can acquire one or more values for two component parts of the complex impedance from signals generated by sensor 66 of tissue sensing circuit 26 (i.e., the resistance (R) and reactance (X) or the impedance magnitude ($|Z|$) and phase angle ($\phi$) or any combination of the foregoing or derivatives or functional equivalents thereof). ECU 32 may combine values for the two components into a single coupling index (ECI) that provides a measure of the degree of coupling between electrode 52 and tissue 12 and, in particular, the degree of electrical coupling between electrode 52 and tissue 12. This process and index are described more fully in commonly assigned U.S. patent application Ser. No. 12/253,637 titled "System and Method for Assessing Coupling Between an Electrode and Tissue" filed Oct. 17, 2008, the entire disclosure of which is incorporated herein by reference. As discussed in that application it should be understood that coefficients, offsets and values within the equation for the coupling index may vary depending on among other things, the desired level or predictability, the species being treated and disease states. Because impedance measurements are also influenced by the design of catheter 16 connection cables 58, 60 or other factors, the coupling index ECI may preferably comprise a flexible equation in which coefficients and offsets are variable in response to design parameters associated with catheter 16. Catheter 16 may include a memory such as an EEPROM that stores numerical values for the coefficients and offsets or stores a memory address for accessing the numerical values in another memory location (either in the catheter EEPROM or in another memory). ECU 32 may retrieve these values or addresses directly or indirectly from the memory and modify the coupling index ECI accordingly. The physical structure of the patient is another factor that may influence impedance measurements and the coupling index. Therefore, ECU 32 may also be configured to offset or normalize the coupling index (e.g., by adjusting coefficients or offsets within the index ECI) responsive to an initial measurement of impedance or another parameter in a particular patient. In addition, it may be beneficial to obtain and average values for the coupling index ECI responsive to excitation signals generated by source 64 at multiple different frequencies. It should be understood that while the coupling index ECI provides a measure of the degree of electrical coupling between electrode 52 and tissue 12, measures of the degree of physical coupling can also be used as a factor in the index CAI including, for example, contact force or contact pressure as noted above.

ECU 32 may maintain, read from and update a data structure containing values for the index CAI and the factors (e.g., RF power, temperature, ECI, etc.) used to determine the index CAI with each index value (and the associated factor values) corresponding to either a discrete location, such as location 76, within volume 74 or a plurality of locations as discussed hereinbelow. ECU 32 continuously calculates and maintains the value of the index CAI for any particular location or group of locations over time such that the index CAI represents an assessment of the instantaneous and cumulative values for the various factors that make up the index. The index CAI may therefore be represented by the following equation:

$$CAI(x, y, z, t) = \int_{t_0}^{t} f(x, y, z, t) dt$$

where x, y, and z represent coordinates for a location 76, t represents time and $f(x,y,z,t)$ is a function g of one or more of the above-described factors. For example, in one embodiment of the invention, the index CAI may be derived from the following function:

$g=\text{ablation\_energy}*ECI$ where ablation_energy represents the amount of ablative energy provided at the location through generator 24 and ECI is an index representative of the degree of electrical coupling between electrode 52 and tissue 12. In another embodiment of the invention, the index CAI may be derived from the following function:

$g=\alpha*\text{ablation\_energy}*ECI+\beta*\text{temperature}$ where $\alpha$ and $\beta$ are constants and temperature represents the temperature proximate the distal end 50 of catheter 16. Each factor in the index CAI may be compared to a threshold value associated with the factor to ensure that any factor forming part of the index CAI is indicative of a predetermined level of ablation therapy at the location (e.g., therapy that will result in irreversible lesions as opposed to brief and reversible exposure of the tissue to ablation). For example, the degree of coupling between electrode 52 and tissue 12 input to the index CAI may be computed as follows:

$ECI=ECI(t)-ECI_{non\text{-}contact}$ where $ECI_{non\text{-}contact}$ represents a threshold value for ECI (typically 100+/−5, whereas ECI is typically between 140 and 180 when in electrode 52 is in moderate contact with tissue 12). Similarly, ablation_energy may be calculated relative to a threshold value intended to compensate for the fact that a very low power level (e.g., 1 watt) will not result in detectable changes to tissue 12:

$\text{ablation\_energy}=\text{ablation\_energy}(t)-1$

Because measured temperatures above the internal body temperature are indicative of effective ablation therapy, a function for determining a temperature value in the index CAI may use body temperature as a threshold value:

$\text{Temperature}=\text{Catheter\_temperature}(t)-\text{Body\_temperature}(t)$ It should be understood that temperature values may also be impacted by irrigation, the flow rate of irrigation fluid and other design parameters for catheter 16 and that the above function could be varied to account for such parameters.

As noted hereinabove, ECU 32 may determine the index (CAI) relative to a discrete location, such as location 76, within the volume 74. In one embodiment of the invention, ECU 32 may further be configured to determine the location not as a discrete value, but rather in response to a plurality of measured positions of catheter 16 over a predetermined period of time. ECU 32 may determine a location by taking, for example, a mean or median value from among a plurality of positions of catheter 16 measured over a time period (e.g., between 0.2 to 2 seconds). ECU 32 may associate the cumulative CAI value over that time period with the determined location. This approach reflects the fact that ablative therapy may be applied to a number of distinct locations that are very close to one another—particularly in short interval.

It should be understood that ECU 32 may calculate values for CAI at location 76 responsive to measurements made at multiple electrodes (e.g., at electrodes 52, 54, 56). For example, the degree of coupling (e.g., electrical coupling or force of contact) between each electrode 52, 54, 56 and tissue 12 can be assessed. Mathematical algorithms (e.g., weighting and interpolation) may be used in connection with the measurements made at the electrodes 52, 54, 56 to derive a more precise assessment of the degree of coupling at location 76 and, consequently, a more precise value of index CAI.

Referring again to FIG. 3, in one embodiment of the invention, ECU 32 is configured to divide the volume 74 into a plurality of volume elements or voxels 78. A data structure is maintained by ECU 32 which correlates instantaneous and cumulative values for the index CAI and the factors used to compute the index with each voxel 78 such that the index CAI and the factors reflect cumulative values taken at a plurality of discrete locations within each voxel 78. In this embodiment, one factor that may be used to compute the index comprises the time in which the ablation catheter 16 is within the voxel as opposed to time spent at a single discrete location. This embodiment of the invention is advantageous given the limitations on providing precise representations of the surface of tissue 12 during mapping and the ability to deliver ablation therapy to discrete locations.

ECU 32 is configured to alter a visual characteristic of voxel 78 responsive to the index CAI. In one embodiment of the invention, the visual characteristic comprises color and, in particular, the intensity of the color. Voxels 78 containing locations 76 where effective ablation therapy is delivered may assume a certain color that becomes more intense or more opaque (illustrated in the drawings by an increase in cross-hatching) as the effectiveness of the therapy increases (as indicated by index CAI). Voxels 78 containing locations where therapy has not been provided or therapy has been relatively ineffective may be transparent or translucent to facilitate the visualization of underlying geometric structures in tissue 12. It should be noted that the visual characteristic does not need to be altered in a linear fashion relative to changes in the index CAI. Various functions may be applied to the index CAI to emphasize specific indices or range of indices likely to represent ineffective ablative therapy. It should also be understood that the visual characteristics of voxel 78 could be altered in response to other factors or measurements in addition to the index CAI. For example, the visual characteristics of voxel 78 may be altered responsive to a measured temperature exceeding a predetermined threshold during ablation such that the appearance of the voxel is altered in multiple ways (e.g, by adjusting the intensity of the color based on index CAI and by alternating between multiple states (i.e., flashing) in the presence of excessive temperatures).

Figure 4:
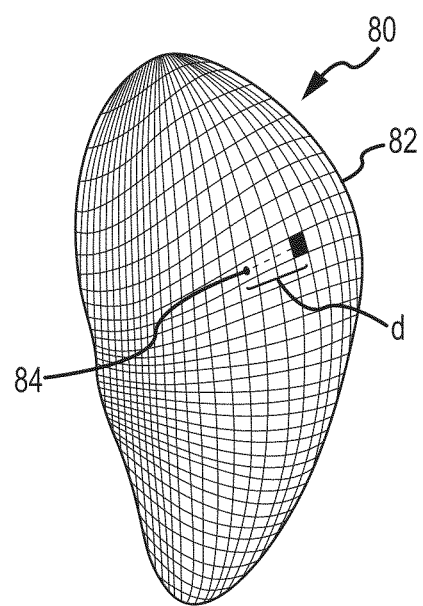
FIG. 4 is a screen display illustrating another embodiment of an anatomical map altered in accordance with the present teachings.

Referring to FIG. 4, in another embodiment of the invention, ECU 32 generates an anatomical map 80 that defines a surface 82. ECU 32 is configured to alter a visual characteristic a portion of the surface 82 responsive to the index CAI and a distance d between a location 84 at which CAI is computed and one or more locations on surface 82 (the relative locations being known by detecting the position of the catheter tip as discussed above and registering the coordinate system with that of map 80 in a conventional manner). ECU 32 may alter surface 82 by again adjusting the color, and particularly the intensity of the color (again illustrated by increased cross-hatching), at the surface 82 or by superimposing a marker (e.g., a disc) thereon. As discussed above, it should be understood that the visual characteristics of surface 82 may also be altered responsive to other factors or measurements in addition to the index CAI Referring again to FIG. 1, display device 34 is provided to display map 72 or 80 and present information permitting the clinician to assess effective delivery of ablation therapy to tissue 12. Device 34 may also provide a variety of information relating to visualization, mapping and navigation as is known in the art including measures of electrical signals, various two and three dimensional images of the tissue 12 and three-dimensional reconstructions of the tissue 12. Device 34 may, for example, display, or combine with map 72 or 80, detailed computed tomography or magnetic resonance images using conventional registration and fusion processes. Device 34 may comprise an LCD monitor or other conventional display device.

I/O device 36 is provided to allow the clinician to control operation of system 30. Device 36 may comprise a keyboard, mouse or other conventional input/output device. In accordance with one aspect of the present invention, device 36 permits the clinician to exercise a measure of control over the computation of index CAI to permit clinicians to provide appropriate weight to those factors the clinician believes are better indicators of effective ablation therapy. ECU 32 is therefore configured to receive a user input through device 36 controlling a weight accorded to at least one of the factors used by ECU to derive index CAI. In this manner, the clinician can, for example, more easily control lesion formation in sensitive areas (e.g., in cardiac tissue near the esophagus).

The above description contemplates review of the altered electroanatomical map 72 or 80 and appropriate adjustment of components of system 10 (e.g., by movement of catheter 16) in response thereto. In an alternative embodiment of the invention, catheter 16 may be controlled automatically (e.g., robotically or magnetically) responsive, in part, to the measured values of CAI. System 30 may obtain measurements and calculate the index CAI. The location of the catheter 16 may be adjusted automatically responsive to the values of CAI using, for example, the robotic or magnetic systems described in commonly assigned U.S. patent application Ser. No. 12/622,488, the entire disclosure of which is incorporated herein by reference. As part of this process, system 30 may identify locations within volume 74 (by altering the visual characteristics of map 72 or 80) that require review, and possibly further treatment, by a clinician.

Referring now to FIG. 5, a series of timing diagrams (in registration with each other) taken during an animal study illustrate changing values over time for several individual factors indicative of the delivery of ablation therapy by a tip electrode 52 at two locations ($x_1, y_1, z_1$) and ($x_2, y_2, z_2$) within cardiac tissue. The first location ($x_1, y_1, z_1$) was in the left atrium while the second location ($x_2, y_2, z_2$) was in the right atrium. The catheter tip was maintained out of contact with the tissue when electrode 52 was at the first location ($x_1, y_1, z_1$) and in moderate contact with the tissue when electrode 52 was at the second location ($x_2, y_2, z_2$). The power level was varied at each location between 1 watt, 20 watts and 40 watts as illustrated in the timing diagram marked "Ablation Power". Although the amount of ablative energy delivered in each location was the same, the catheter tip temperature, the electrical coupling index (ECI) (as well as its individual component parts R1 and X1) and other values remained relatively constant over the time period in which the electrode 52 was at the first location ($x_1, y_1, z_1$) and varied considerably during the timer period in which the electrode 52 was the second location ($x_2, y_2, z_2$). Similarly, the index CAI remained relatively constant during the time period the electrode 52 was at the first location ($x_1, y_1, z_1$) and varied during the time period in which the electrode 52 was at the second location ($x_2, y_2, z_2$) to indicate more effective delivery of ablation therapy. In the illustrated embodiment, CAI was calculated from the following equation:

$$CAI = 0.025 * (ECI - 90) * (\text{ablation\_energy} - 3.4) + 2 * (\text{temperature} - 37)$$

With ECI, ablation_energy, and temperature all compared to threshold values such that each factor impacts CAI only if it is indicative of a predetermined level of ablation therapy at the location (e.g., therapy that will result in irreversible lesions as opposed to brief and reversible exposure of the tissue to ablation)

In summary, the effective delivery of ablation therapy to tissue 12 is assessed through several method steps in accordance with one embodiment of the present invention. First, a three-dimensional anatomical map 72 or 80 of the tissue 12 is generated. The map may be generated by ECU 32 in a conventional manner using values measured from the movement of a conventional mapping catheter or may be based on a real-time image such as an ultrasound image or fluoroscopic image or a pre-acquired image (e.g., an image generated by an MRI, CT, ultrasound or fluoroscopic system). The map 72 or 80 is then displayed on, for example, a conventional display device 34. ECU 32 then generates an index CAI corresponding to a location 76 or 84 within a volume 74 or 82 defined by the map 72 or 80, respectively. The index CAI is indicative of a state of ablation therapy at the location. Finally, a visual characteristic of a portion of the map 72 or 80 corresponding to the location 76 or 84 is altered responsive to the index.

A system and method in accordance with the present teachings offers one or more of a number of advantages. The system and method provide a less subjective and more accurate map of ablation lesions than conventional systems and methods. The use of an index based on one or more factors or predictors indicative of the state of ablative therapy provides a more objective assessment of the effective delivery of ablation therapy while reducing the impact of variabilities such as catheter or tissue movement or changes in operating conditions. As a result, clinicians can assess the effectiveness of ablation therapy with greater confidence and reduce or eliminate the need for electrophysiologic mapping procedures and repeated ablation.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for assessing effective delivery of ablation therapy to a tissue in a body, comprising:
    an electronic control unit configured to generate a three-dimensional anatomical map of said tissue, said map defining a corresponding volume; and,
    a display configured to display said anatomical map;
    wherein said electronic control unit is further configured to generate an index corresponding to a first location within said volume, said index indicative of a state of ablation therapy at said first location, and to alter, responsive to said index, a visual characteristic of a portion of said anatomical map corresponding to said first location; and
    wherein said index is generated responsive to a factor indicative of delivery of ablative therapy to said tissue only when a value of said factor exceeds a threshold value associated with said factor.

2. The system of claim 1 wherein said volume is divided into a plurality of voxels and said portion of said anatomical map comprises a first voxel of said plurality of voxels, said first location within said first voxel.

3. The system of claim 1 wherein said electronic control unit is further configured to determine a position of an ablation catheter and to determine said first location responsive to a plurality of positions of said ablation catheter over a predetermined period of time.

4. The system of claim 1 wherein said visual characteristic comprises a color.

5. The system of claim 4 wherein said visual characteristic comprises an intensity of said color.

6. The system of claim 1 wherein said electronic control unit is further configured to adjust a weight accorded to said factor responsive to a user input.

7. The system of claim 1 wherein said index is generated responsive a to a duration of time during which ablation energy is provided at said first location.

8. The system of claim 1 wherein said index is generated responsive to an amount of ablation energy provided at said first location.

9. The system of claim 1 wherein said index is generated responsive to a degree of contact between an ablation electrode and said tissue.

10. The system of claim 1 wherein said index is generated responsive to a degree of electrical coupling between an ablation electrode and said tissue.

11. The system of claim 1 wherein said index is generated responsive to a temperature proximate said first location.

12. A method for assessing effective delivery of ablation therapy to a tissue in a body, comprising:
    generating a three-dimensional anatomical map of said tissue, said map defining a corresponding volume;
    displaying said anatomical map;
    analyzing a plurality of factors indicative of a state of ablation therapy at a first location within said volume;
    comparing each factor against an associated threshold value;
    updating an index corresponding to the first location within said volume, if at least one of said factors exceeds the associated threshold value; and,
    altering, responsive to said index, a visual characteristic of a portion of said anatomical map corresponding to said first location.

13. The method of claim 12, further comprising the step of adjusting a weight accorded to at least one of said factors responsive to a user input.

14. The method of claim 12 wherein said index is generated responsive to an amount of ablation energy provided at said first location.

15. The method of claim 12 wherein said index is generated responsive to a degree of contact between an ablation electrode and said tissue.

16. The method of claim 12 wherein said index is generated responsive to a degree of electrical coupling between an ablation electrode and said tissue.

17. The method of claim 12 wherein said index is generated responsive to a temperature proximate a tip of an ablation catheter.

18. The method of claim 12 wherein said index is generated responsive to an electrical coupling index (ECI).

19. A system for assessing effective delivery of ablation therapy to a tissue in a body, comprising:
    an electronic control unit configured to generate a three-dimensional anatomical map of said tissue, said map defining a corresponding volume; and,
    a display configured to display said anatomical map;
    wherein said electronic control unit is further configured to:
        receive a plurality of weighted factors indicative of a state of ablation therapy at a first location within said volume;
        adjust at least one of the plurality of weighted factors responsive to a user input;
        generate an index indicating a state of the ablation therapy at the first location; and
        alter, responsive to said index, a visual characteristic of a portion of said anatomical map corresponding to said first location.

* * * * *